United States Patent [19]

Palmquist et al.

[11] Patent Number: 4,642,317

[45] Date of Patent: Feb. 10, 1987

[54] PROCESS FOR FEEDING RUMINANT ANIMALS AND COMPOSITION FOR USE THEREIN

[75] Inventors: Donald L. Palmquist, Wooster; Thomas C. Jenkins, Apple Creek, both of Ohio

[73] Assignee: The Ohio Agricultural Research and Development Center, Wooster, Ohio

[21] Appl. No.: 567,617

[22] Filed: Jan. 3, 1984

Related U.S. Application Data

[63] Continuation of Ser. No. 274,145, Jun. 16, 1981, abandoned.

[51] Int. Cl.$^4$ ............................................. A61K 31/20
[52] U.S. Cl. ..................................... 514/558; 514/560
[58] Field of Search ................................. 424/317, 318

[56] References Cited

U.S. PATENT DOCUMENTS

| 2,182,171 | 12/1939 | Coyner | 424/317 |
| 2,831,769 | 4/1958 | Kamlet | 424/318 |
| 2,899,308 | 8/1959 | Ely et al. | 424/318 |
| 3,222,179 | 12/1965 | Schöner | 424/317 |
| 3,458,625 | 7/1969 | Ensor et al. | 424/318 |
| 3,569,098 | 2/1971 | Erwin et al. | 424/317 |

FOREIGN PATENT DOCUMENTS 736940  7/1980  U.S.S.R. .

OTHER PUBLICATIONS

Palmquist, et al.—Journal of Diary Science, vol. 63, No. 1, Jan. 1980, pp. 1-14.
Jenkins & Palmquist, Journal of Dairy Science, 67, 978 (1984).

Primary Examiner—Frederick E. Waddell
Attorney, Agent, or Firm—Sidney W. Millard

[57] ABSTRACT

A process and composition for supplying fatty acids to ruminants comprising feeding the fatty acids to the ruminants in the form of their calcium salts. The calcium salts may be added to conventional cattle feed preferably in an amount not exceeding about 5% of the dry solids content of the feed.

15 Claims, No Drawings

PROCESS FOR FEEDING RUMINANT ANIMALS AND COMPOSITION FOR USE THEREIN

This application is a continuation of our application Ser. No. 06/274,145, filed June 16, 1981 and now abandoned.

BACKGROUND OF THE INVENTION

The invention relates to a process of feeding ruminant animals and to a composition for use therein. More specifically, the invention relates to a process and composition which allows ruminant animals to be fed increased amounts of fat in their diet without deleterious effects on the microorganism populations within the ruminants' stomachs.

Conventional cattle feeds, such as corn and alfalfa, often fail to provide sufficient energy for cattle, especially lactating dairy cattle during periods of heavy milk production. Feed containing a high proportion of corn also has a tendency to depress the milk fat content of the milk produced by such cattle. Fat (a term which is used herein to include both fats which are solid and oils which are liquid at ambient temperature, and includes material from both animal and vegetable sources) is an excellent energy source, and it has been suggested that if the proportion of fat in cattle food could be increased, lactating dairy cattle could produce high milk yields without draining their reserves of body fat and without diminishing the proportion of milk fat in the milk produced.

Large quantities of fat are available commercially as a by-product of the meat packing, fast food and other industries, and this waste fat has already been successfully used in poultry rations. However, although poultry can metabolize fat without any undesirable side effects, it has been found that if the proportion of fat in the diet of cattle exceeds about 2% of the total feed solids, the feed has toxic effects upon the microorganisms in the rumen of the cattle. It appears that fat reduces the growth rate or even kills certain microorganisms which digest fiber in the cow's rumen, thereby lowering fiber digestibility. This deleterious effect on the cow's rumen is particularly true of unsaturated fats. Although the decreased fiber digestion in the rumen is partially compensated by greater fiber digestion in the lower parts of the alimentary canal, such later fiber digestion produces a blend of different fatty acids than that which is produced by the digestion in the rumen and the different blend of fatty acids is less suited to the cow's metabolism.

It has previously been proposed to feed fatty acids to cattle in an encapsulated form in order to avoid the aforementioned effects on the cattle's rumens. Encapsulation techniques previously proposed include coating the fat particles with a protein which is then cross-linked with formaldehyde. However, formaldehyde has many undesirable physiological effects and the potential health threat to both cattle and humans from including formaldehyde in cattle feed prevents such formaldehyde-protein encapsulated fat being used in commercial dairy herds.

There is thus a need for a process whereby fats, or at least the essential dietary constituents thereof, i.e. fatty acids, can safely be fed to ruminant animals without interfering with the animals' rumens' microorganism population. The instant invention provides such a method.

SUMMARY OF THE INVENTION

The invention provides a process for supplying a fatty acid to ruminant animals which comprises feeding the fatty acid to the animals in the form of its calcium salt, said salt being fed to said animals in an amount of at least about 1% of the dry solids weight of their feed. The process is mainly intended for use in cattle, especially lactating dairy cattle.

The invention also provides a cattle feed comprising at least one vegetable material such as legume hay, grass hay, corn silage, grass silage, legume silage, corn grain, oats, barley, distillers' grain, brewer's grain, soya bean meal and cotton seed meal, and at least about 1% by weight on a dry solids basis, of a calcium salt of a fatty acid.

DETAILED DESCRIPTION OF THE INVENTION

In the process of the instant invention, the calcium fatty acid salt may conveniently be fed to the cattle admixed with a conventional cattle feed. Desirably, the amount of calcium fatty acid salt in such a feed admixture does not exceed about 10% of the dry solids content of the feed and is preferably about 3–5% of the dry solids content of the feed. There is no particular lower limit for the amount of calcium fatty acid salt to be added to the cattle feed, although in practice amounts of the calcium salt below about 1% of the dry solids content of the feed are too small to provide significant amounts of energy to the cattle. It is known to feed small amounts (about 20 gms./day) of calcium stearate to cattle as a supposedly inert protective agent for certain feed supplements such as methionine. However, the amounts of calcium stearate fed to cattle in this manner are much smaller than those used in the instant process.

The calcium fatty acid salt fed to the cattle in the instant process may be the salt of a single pure fatty acid such as stearic acid. However, it will be found more economical to use a mixture of calcium fatty acid salts derived from a natural fat; for example, tallow. Not only is it cheaper to prepare a mixed calcium fatty acid salt from such a natural fat, but such a natural mixture is likely to be more easily metabolized by the animal's system; it appears, for example, that the use of pure calcium stearate does not lead to very efficient absorption of stearic acid by the animal. Preferably, the calcium fatty acid salt has an analysis substantially within the following ranges by weight:

| | |
|---|---|
| 16:0 | 0–50% |
| 18:0 | 0–50% |
| 18:1 | 0–100% |
| 18:2 | 0–60% |

In addition, the 18:3 fraction (linolenic acid) content should be less than about 10% by weight since larger amounts of linolenic or other highly unsaturated fatty acids, when incorporated into the milk fat produced by the animal, cause formation of peroxides in the milk which cause the milk to turn rancid very quickly. It will, of course, be appreciated that the calcium salts used in the instant process may be derived from fatty acids other than those specifically mentioned (for example, myristic (14:0) acid). However, the fatty acids should be similar to those found in natural fats and oils and thus should contain at least 10 carbon atoms.

The calcium fatty acid salts used in the instant process are known compounds and some of them, for example calcium stearate, are available commercially, being used as solid lubricants and mold release compounds. However, the synthesis of such calcium salts from naturally occurring oils and fats presents no problems to those of ordinary skill in the chemical art. For example, the fat or oil may be saponified in the conventional manner with sodium or potassium hydroxide and the resulting sodium or potassium salt separated from the glycerol-containing liquor. The formed sodium or potassium salt is then dissolved in an aqueous solution and mixed with an aqueous solution of a calcium salt (calcium chloride being preferred for the sake of cheapness and solubility), whereupon metathesis takes place and the substantially water-insoluble calcium fatty acid salt precipitates out and may be filtered off.

It is not necessary that the calcium salt used in the instant process be completely free of free fatty acid or traces of the original fat, but in order to prevent problems with disturbance of the rumen microorganism population, at least 95% of the fatty acid in the product should be in the form of the calcium salt. The water content of the calcium salt is desirably less than about 15%, since higher water contents introduce undesirably large amounts of water into the feed, which may cause problems with mold growth thereon.

It is believed (although the invention is in no way limited by this belief) that the reason why the calcium salts permit efficient uptake of fatty acid from the feed without disturbing the rumen microorganism population is that the calcium salts are insoluble in the rumen, thus "by-passing" this fermentation system and avoiding disturbance of the microorganism population therein, but are solubilized in the acid environment of the abomasum and the first part of the small intestine, thus making both calcium and fatty acids available for absorption. The calcium appears to be preferably absorbed from the acid in the first part of the small intestine, leaving the fatty acid to be absorbed further down the alimentary canal.

It should be noted that the advantages secured by the use of calcium fatty acid salts in the feed are *not* secured when the animals are fed a mixture of fat and either an insoluble calcium salt such as limestone or a soluble calcium salt such as calcium chloride. Experiments we have conducted using cattle having fistulated rumens permitting direct sampling of the rumen contents indicate that if the animal is fed a mixture of fat and a soluble calcium salt, only a minor proportion of the fat is converted to calcium fatty acid salts in the rumen, and the remaining major proportion of unchanged fat in the rumen still interferes with the rumen microorganism population and thus with fiber digestion. Furthermore, if a typical fat containing both saturated and unsaturated acids is fed to a cow together with a soluble calcium salt, the saturated fatty acids react preferentially with the calcium salts, leaving a high concentration of free unsaturated fatty acids in the rumen, and, as noted above, free unsaturated fatty acids have especially undesirable effects upon rumen metabolism.

Since cattle usually consume about 20 kg. of feed per day (on a dry solids basis), if 5% of the calcium fatty acid salts are included in the diet, the cattle will consume about 1 kg/animal/day of the calcium salt. Thus each animal will ingest about 100 gm/day of calcium from the fatty acid. This is about the same amount of calcium which is normally given to lactating animals in their mineral supplement, and if desired, the amount of calcium in the mineral supplement may be reduced since the cattle will receive sufficient calcium from the fatty acid salt.

The following examples are now given, though by way of illustration only, to show details of particularly preferred compositions and processes of the instant invention.

EXAMPLE 1

A grain supplement was prepared having the following constitution:

|  | % | Pounds |
| --- | --- | --- |
| Corn, ¼" grind | 46.6 | 466.0 |
| Wheat middlings | 20.0 | 200.0 |
| Soybean meal | 19.6 | 196.0 |
| Calcium soap (dry weight of tallow fatty acids) | 11.1 | 111.0 |
| Hydan (Hydroxy methionine analog) | 0.3 | 3.0 |
| Dicalcium phosphate | 0.7 | 7.0 |
| Magnesium oxide | 0.2 | 2.0 |
| Salt, trade mineralized | 1.0 | 10.0 |
| Selenium premix | 0.1 | 1.0 |
| Vitamin A | 0.1 | 1.0 |
| Vitamin D | 0.1 | 1.0 |
| Vitamin E | 0.2 | 2.0 |
|  | 100.0 | 1000.0 |

This grain supplement was then used as 40% (on a dry matter basis) of a cattle feed, the remaining 60% of the feed being composed of equal amounts by weight of hay silage and corn silage. The resultant feed, containing about 4.4% (on a dry matter basis) of calcium tallow fatty acids salt proved highly acceptable to lactating dairy cattle.

EXAMPLE 2

Feeding Trials

A grain mix was prepared having the following constitution:

|  | % by weight on dry matter basis |
| --- | --- |
| Ground corn | 58.6 |
| Rolled oats | 13.0 |
| Soya bean meal | 25.0 |
| Dicalcium phosphate | 1.0 |
| Limestone | 1.0 |
| Salt, trace mineralized | 1.0 |
| Vitamin A | 0.09 |
| Vitamin D | 0.01 |
| Vitamin E | 0.1 |
| Selenium pre-mix | 0.25 |

The above grain mix was then mixed with various additives to prepare the following grain mixes:

A: No additives (Control)
B: 10% by weight of tallow fat absorbed on half its weight of Verxite (an inert carrier material) (Control)
C: ~11% by weight of calcium salts of tallow fatty acids to provide 10% by weight of fatty acid
D: ~11% of calcium salts of vegetable fatty acids, to provide 10% by weight of fatty acid
E: 10% by weight of free tallow fatty acids (Control)
F: 10% by weight of free vegetable fatty acids (Control)

Each of the grain mixes A-F was then mixed in a complete ration having a 1:2:3 ratio (on a wet basis) of long alfalfa hay:grain mix:corn silage (equivalent to about 1:2:1 on a dry matter basis). The rations were fed to six lactating Holstein dairy cows in a 6×6 Latin square arrangement as follows, each cow being fed each ration for a period of two weeks.

| PERIOD | COW | | | | | |
|---|---|---|---|---|---|---|
| | 2433 | 2441 | 2452 | 2531 | 2533 | 2542 |
| (1) 6/9-6/21 | A | B | C | D | E | F |
| (2) 6/21-7/5 | B | C | D | E | F | A |
| (3) 7/5-7/19 | C | D | E | F | A | B |
| (4) 7/19-8/2 | D | E | F | A | B | C |
| (5) 8/2-8/16 | E | F | A | B | C | D |
| (6) 8/16-8/30 | F | A | B | C | D | E |

During the last 5 days of each period, each cow was subjected to a total collection digestion trial in which digestibility co-efficients were determined for acid detergent fiber (ADF), dry matter (DM), Ca, Mg, P and N. Also determined were daily milk yield, dry matter intake, percent ADF in refused feed and percent milk fat in milk produced. The following results were obtained:

It will be noted that diets B-F each contained 5% fatty acids on a dry matter basis.

The combined results obtained on all six cows using the control diet A and the diets B, E and C containing the three forms of tallow fatty acids are summarized in Tables 1 and 2:

TABLE 1
EFFECT OF VARIOUS FORMS OF TALLOW FATTY ACIDS ON FEED CONSUMPTION AND MILK CONSUMPTION

| | DIET | | | |
|---|---|---|---|---|
| | A | B | E | C |
| Feed dry matter intake, kg/day | 14.6 | 13.9 | 13.4 | 12.5 |
| Milk, kg/day | 18.3 | 17.9 | 18.6 | 17.3 |
| Milk fat, % | 3.67 | 3.61 | 3.52 | 3.51 |

TABLE 2
EFFECT OF VARIOUS FORMS OF TALLOW FATTY ACIDS ON NUTRIENT DIGESTIBILITY (%)

| Digestibility co-efficient | DIET | | | |
|---|---|---|---|---|
| | A | B | E | C |
| Dry matter | 70.0 | 67.6 | 70.2 | 68.7 |
| Acid detergent fiber | 51.5 | 51.2 | 44.9* | 49.6 |
| Nitrogen | 62.4 | 63.8 | 65.8 | 61.6 |
| Calcium | 30.8 | 24.6 | 29.0 | 18.2* |
| Magnesium | 27.6 | 28.0 | 18.7 | 15.6** |
| Phosphorous | 35.6 | 30.9 | 36.6 | 30.9 |

*Significantly lower than other treatments (P < .10).
**Significantly lower than other treatments (P < .05)

DIGESTIBILITY COEFFICIENTS

| Diet | Cow | Period | ADF | DM | Ca | Mg | P | N | Milk Yield kg/day | DM Intake kg/day | % ADF refusal | % milk fat |
|---|---|---|---|---|---|---|---|---|---|---|---|---|
| A | 2433 | 1 | 56.6 | 72.9 | 42.9 | 32.7 | 33.7 | 59.5 | 10.0 | 17.4 | 51.3 | N/T |
| A | 2441 | 6 | 52.0 | 67.6 | 28.9 | 29.3 | 36.0 | 61.6 | 17.9 | 15.3 | 49.3 | 3.39 |
| A | 2452 | 5 | 52.6 | 69.7 | 50.7 | 27.6 | 38.0 | 62.0 | 20.5 | 15.1 | 31.0 | 3.01 |
| A | 2531 | 4 | 45.3 | 69.6 | 32.3 | 27.3 | 38.1 | 66.9 | 19.9 | 13.6 | 39.0 | 3.70 |
| A | 2533 | 3 | 42.4 | 69.6 | 5.0 | 22.2 | 32.7 | 61.2 | 18.0 | 10.7 | 34.7 | 3.66 |
| A | 2542 | 2 | 60.2 | 70.6 | 24.8 | 26.6 | 34.9 | 63.0 | 15.3 | 15.4 | 43.9 | 4.49 |
| B | 2433 | 2 | 56.5 | 68.9 | 31.8 | 37.5 | 34.7 | 70.0 | 7.5 | 15.3 | 35.9 | 3.21 |
| B | 2441 | 1 | 41.8 | 64.9 | 29.2 | 25.5 | 29.3 | 48.5 | 20.1 | 16.2 | 47.2 | N/T |
| B | 2452 | 6 | 60.6 | 71.5 | 33.3 | 41.4 | 46.7 | 71.5 | 19.0 | 16.1 | 38.1 | 3.17 |
| B | 2531 | 5 | 55.8 | 67.4 | 27.9 | 5.1 | 16.8 | 65.2 | 18.1 | 11.8 | 31.1 | 3.36 |
| B | 2533 | 4 | 43.8 | 68.0 | 23.5 | 27.5 | 31.8 | 66.0 | 17.0 | 11.9 | 40.1 | N/T |
| B | 2542 | 3 | 48.6 | 65.1 | 2.0 | 31.1 | 26.3 | 61.6 | 15.5 | 12.3 | 45.6 | 5.17 |
| C | 2433 | 3 | 55.2 | 70.3 | 18.5 | 3.3 | 26.3 | 66.7 | 4.4 | 12.1 | 39.5 | 3.58 |
| C | 2441 | 2 | 52.2 | 67.2 | 16.4 | 18.3 | 35.0 | 68.0 | 19.2 | 14.9 | 36.8 | 2.85 |
| C | 2452 | 1 | 48.5 | 73.0 | 12.2 | 19.1 | 30.3 | 55.9 | 23.7 | 15.0 | 44.5 | N/T |
| C | 2531 | 6 | 37.0 | 61.0 | 12.1 | 1.4 | 24.4 | 51.3 | 13.2 | 7.9 | 18.9 | 3.45 |
| C | 2533 | 5 | 46.7 | 69.0 | 18.4 | 20.3 | 28.6 | 64.2 | 13.7 | 9.6 | 29.6 | 3.56 |
| C | 2542 | 4 | 57.8 | 71.6 | 31.6 | 31.2 | 41.0 | 63.4 | 16.8 | 15.6 | 36.3 | 4.26 |
| D | 2433 | 4 | 51.7 | 70.7 | 27.6 | 26.5 | 22.7 | 64.7 | 1.3 | 11.6 | 40.3 | 3.94 |
| D | 2441 | 3 | 52.7 | 69.6 | 30.4 | 20.4 | 29.5 | 64.1 | 17.3 | 13.2 | 20.7 | 3.42 |
| D | 2452 | 2 | 60.2 | 68.8 | 27.5 | 29.2 | 42.7 | 67.9 | 23.7 | 15.2 | 26.4 | 2.88 |
| D | 2531 | 1 | 62.3 | 75.6 | 37.5 | 11.4 | 38.2 | 63.6 | 51.9 | 14.7 | 39.2 | N/T |
| D | 2533 | 6 | 51.4 | 70.4 | 31.8 | 52.3 | 30.4 | 65.9 | 12.0 | 10.9 | 32.0 | 3.30 |
| D | 2542 | 5 | 54.7 | 69.2 | 27.4 | 4.2 | 31.6 | 60.8 | 16.4 | 12.5 | 18.8 | 4.20 |
| E | 2433 | 5 | 52.3 | 70.8 | 27.5 | 13.3 | 8.6 | 72.2 | .5 | 12.8 | 30.3 | 3.78 |
| E | 2441 | 4 | 29.8 | 67.6 | 23.1 | 26.9 | 38.4 | 66.0 | 19.3 | 12.8 | 35.4 | 2.52 |
| E | 2452 | 3 | 55.7 | 72.3 | 29.5 | 27.6 | 46.1 | 73.8 | 19.3 | 14.8 | 25.0 | 3.78 |
| E | 2531 | 2 | 52.3 | 71.6 | 36.5 | 18.8 | 50.0 | 73.1 | 21.1 | 13.4 | 28.8 | 3.01 |
| E | 2533 | 1 | 35.6 | 69.8 | 33.7 | 7.9 | 38.5 | 46.2 | 17.6 | 12.3 | 35.9 | N/T |
| E | 2542 | 6 | 43.7 | 69.3 | 23.6 | 17.9 | 37.8 | 63.2 | 15.9 | 14.3 | 47.7 | 4.60 |
| F | 2433 | 6 | 58.6 | 73.4 | 33.9 | 43.6 | 72.2 | 69.6 | N/T | 12.9 | 28.6 | 3.58 |
| F | 2441 | 5 | 40.4 | 67.7 | 42.2 | 23.9 | 66.0 | 69.2 | 19.3 | 14.3 | 41.7 | 1.97 |
| F | 2452 | 4 | 53.1 | 72.0 | 38.8 | 42.4 | 73.8 | 69.3 | 20.9 | 15.1 | 29.7 | 4.15 |
| F | 2531 | 3 | 49.0 | 65.5 | −9.5 | −2.4 | 73.1 | 58.9 | 18.9 | 11.3 | 17.2 | 3.31 |
| F | 2533 | 2 | 61.2 | 73.6 | 42.2 | 48.0 | 46.2 | 68.5 | 17.6 | 13.8 | 30.7 | 3.01 |
| F | 2542 | 1 | 44.7 | 68.6 | 22.0 | 26.8 | 63.2 | 49.3 | 17.3 | 16.5 | 34.1 | N/T |

N/T = not tested

Although the yields of milk were low, partly because the cows were restrained in stalls, Table 1 shows that the various forms of tallow fatty acids had no significant effect on either milk yield or milk fat content. The diet E containing unesterified fat significantly depressed acid detergent fiber digestibility where the ADF digestibility achieved using the calcium salt (diet C) was not significantly different from the added fat-free diet A.

EXAMPLE 3

Feeding Trials

Two steers, each provided with a duodenal cannula, were fed for two week periods with (a) a 50-50 control diet of orchard grass hay; grain concentrate, (b) the same diet but with 5% of the dry matter replaced with tallow fatty acids; and (c) the same diet but with 5% of the dry matter replaced with calcium salts of tallow fatty acids. During the last five days of each 14-day feeding period, the feed particulate material was labelled with radioactive ytterbium ($^{169}$Yb) to measure the flow of feed ingested. During the last 48 hours of each feeding period, duodenal contents were sampled at 30 minute intervals. The following rumen and digestability co-efficients were obtained (combining the results from the two steers):

TABLE 3

RUMEN AND TOTAL DIGESTIBILITY OF FEEDS CONTAINING TALLOW FATTY ACIDS OR SOAPS

| | % Digestibility | | | | | |
|---|---|---|---|---|---|---|
| Diet | Rumen | | | Total | | |
| Feed Fraction | (a) | (b) | (c) | (a) | (b) | (c) |
| Dry Matter | 41.8 | 29.2 | 44.1 | 71.6 | 71.7 | 69.8 |
| Acid Detergent fiber | 54.4 | 27.3 | 56.1 | 56.0 | 51.3 | 53.4 |
| Neutral Detergent fiber | 52.6 | 35.8 | 58.6 | 63.4 | 58.9 | 58.3 |
| Fatty Acids | −2.3 | 3.3 | 32.0 | 55.9 | 81.3 | 76.4 |

It will be seen that diet (b) containing free fatty acids sharply reduced rumen digestibility of the dry matter and fiber fractions although it had little effect on total digestibility. The reduction of rumen digestibility caused by the free fatty acids was completely eliminated by feeding the fatty acids in the form of their calcium salts. As previously noted, the reduction in rumen digestibility of fiber caused by free fatty acids is deleterious even if total digestibility remains unchanged since the blend of fatty acids produced by hind-gut digestion is not as advantageous to the cow as that produced by rumen digestion.

It will be apparent to those skilled in the art that numerous changes and modifications may be made without departing from the scope of the invention. Accordingly, the foregoing description is to be interpreted in an illustrative and not in a limitive sense, the scope of the invention being defined solely by the appended claims.

We claim:

1. A process for supplying a fatty acid containing at least 10 carbon atoms to ruminant animals which comprises feeding to said animals the calcium salt of said fatty acid in an amount equal to at least about 1% of the dry matter content of said animals' feed.

2. A process according to claim 1 wherein said animals are cattle.

3. A process according to claim 2 wherein said animals are lactating dairy cattle.

4. A process according to claim 2 wherein said calcium fatty acid salt is fed to said cattle admixed with a conventional cattle feed.

5. A process according to claim 4 wherein said calcium fatty acid salt is added to said feed in an amount not exceeding about 10% of the dry matter content of said feed.

6. A process according to claim 5 wherein said calcium fatty acid salt is added to said feed in an amount of about 3 to about 5% of the dry matter content of said feed.

7. A process according to claim 5 wherein said calcium fatty acid salt is added to said feed in an amount of about 5% of the dry matter content of said feed.

8. A process according to claim 1 wherein said calcium fatty acid salt has an analysis substantially within the following ranges by weight:

| 16:0 | 0–50% |
|---|---|
| 18:0 | 0–50% |
| 18:1 | 0–100% |
| 18:2 | 0–60% |
| 18:3 | Less than 10%. |

9. A process according to claim 1 wherein said calcium salt is in a form containing not more than about 15% of water.

10. A cattle feed comprising at least one vegetable material edible by ruminants and selected from the group consisting of legume hay, grass hay, corn silage, grass silage, legume silage, corn grain, oats, barley, distiller's grain, brewer's grain, soya bean meal and cotton seed meal, and a calcium salt of a fatty acid containing at least 10 carbon atoms, said calcium salt comprising at least about 1% of the dry matter content of said feed, at least about 95% of the fatty acid in said feed being in the form of the calcium salt.

11. A cattle feed according to claim 10 wherein said calcium fatty acid salt is present in an amount of not more than about 10% of the dry solids content of said feed.

12. A cattle feed according to claim 11 wherein said calcium fatty acid salt is present in an amount of about 3 to about 5% of the dry matter content of said feed.

13. A cattle feed according to claim 12 wherein said calcium fatty acid salt is present in an amount of about 5% of the dry matter content of said feed.

14. A cattle feed according to claim 11 wherein said calcium fatty acid salts have an analysis substantially within the following ranges by weight:

| 16:0 | 0–50% |
|---|---|
| 18:0 | 0–50% |
| 18:1 | 0–100% |
| 18:2 | 0–60% |
| 18:3 | Less than 10%. |

15. A cattle feed according to claim 11 wherein said calcium fatty acid salt is in a form containing not more than about 15% of water.

* * * * *

REEXAMINATION CERTIFICATE (3087th)
United States Patent [19]
Palmquist et al.

[11] B1 4,642,317
[45] Certificate Issued Dec. 31, 1996

[54] PROCESS FOR FEEDING RUMINANT ANIMALS AND COMPOSITION FOR USE THEREIN

[75] Inventors: Donald L. Palmquist, Wooster; Thomas C. Jenkins, Apple Creek, both of Ohio

[73] Assignee: Ohio Agricultural Research and Development Center, Wooster, Ohio

Reexamination Requests:
No. 90/003,412, Apr. 29, 1994
No. 90/003,537, Aug. 23, 1994
No. 90/003,579, Sep. 19, 1994

Reexamination Certificate for:
Patent No.: 4,642,317
Issued: Feb. 10, 1987
Appl. No.: 567,617
Filed: Jan. 3, 1984

Related U.S. Application Data

[63] Continuation of Ser. No. 274,145, Jun. 16, 1981, abandoned.

[51] Int. Cl.⁶ .................................................. A61K 31/20
[52] U.S. Cl. ...................................... 514/558; 514/560
[58] Field of Search ............................ 514/2, 558, 560; 426/2

[56] References Cited

U.S. PATENT DOCUMENTS

| | | | |
|---|---|---|---|
| 2,182,171 | 12/1939 | Coyner | 167/53 |
| 2,831,769 | 4/1958 | Kamlet | 99/2 |
| 2,899,308 | 8/1959 | Ely et al. | 99/4 |
| 3,051,571 | 8/1962 | Pergament | 99/2 |
| 3,222,179 | 12/1965 | Schoner | 99/2 |
| 3,420,672 | 1/1969 | Appleman | 99/6 |
| 3,458,625 | 7/1969 | Ensor et al. | 424/95 |
| 3,959,493 | 5/1976 | Baalsrud et al. | 426/2 |
| 4,062,988 | 12/1977 | De Santis | 426/656 |
| 4,153,735 | 5/1979 | Mommer | 426/285 |
| 4,221,818 | 9/1980 | Schroeder | 426/138 |
| 4,642,317 | 2/1987 | Palmquist et al. | 514/558 |
| 4,826,694 | 5/1989 | McAskie | 426/74 |

FOREIGN PATENT DOCUMENTS

| | | |
|---|---|---|
| 736940 | 5/1980 | U.S.S.R. |
| 852189 | 10/1960 | United Kingdom |
| 1045704 | 10/1966 | United Kingdom |
| 1387038 | 3/1975 | United Kingdom |
| 2113521 | 8/1983 | United Kingdom |

OTHER PUBLICATIONS

Bines, J. A. et al., "The effect of protected lipids on nutrient intakes, blood and rumen metabolites and milk secretion in dairy cows during early lactation", J. Agric. Sci. Camb., 91, 135–150 (1978).

Brumby, P. E., et al., "Utilization of energy for maintenance and production in dairy cows given protected tallow during early lactation", J. Agric. Sci. Camb., 91, 151–159 (1978).

Galbraith, H., et al., "Antibacterial Activity of Long Chain Fatty Acids and the Reversal with Calcium, Magnesium, Ergocalciferol and Cholesterol", J. Appl. Bact., 34(4), 803–813 (1971).

El Hag, G. A., et al., "Evaluation of Whisky Distillery By-products", J. Sci. Fd Agric., 23, 247–258 (1972).

Hawley, G. G., The Condensed Chemical Dictionary, 9th Edition, published by Van Nostrand Reinhold Company, pp. 781–782 (1977).

Palmquist, D. L., et al., "Fat in Lactation Rations: Review", Journal of Dairy Science, vol. 63, No. 1., pp. 1–14 (1980).

Pattison, E. S., ed., Fatty Acids and Their Industrial Applications, published by Marcel Dekker, Inc., pp. 209–220 (1968).

Scott, T. W., et al., "Protection of Dietary Polyunsaturated Fatty Acids Against Microbial Hydrogenation in Ruminants", Journal of the American Oil Chemists' Society, vol. 48, pp. 358–364 (1970).

Ohio Agricultural Research and Development Center, "They're Feeding Soap to Dairy Cows", Press Release (1980).

*Primary Examiner*—Raymond J. Henley, III

[57] ABSTRACT

A process and composition for supplying fatty acids to ruminants comprising feeding the fatty acids to the ruminants in the form of their calcium salts. The calcium salts may be added to conventional cattle feed preferably in an amount not exceeding about 5% of the dry solids content of the feed.

REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1–15 are cancelled.

* * * * *